(12) United States Patent
Maesani et al.

(10) Patent No.: US 11,266,835 B2
(45) Date of Patent: Mar. 8, 2022

(54) ELECTRICAL STIMULATOR FOR NEUROMUSCULAR STIMULATION

(71) Applicant: MINDMAZE HOLDING SA, Lausanne (CH)

(72) Inventors: Andrea Maesani, Lausanne (CH); Andrea Biasiucci, Ecublens (CH)

(73) Assignee: MINDMAZE HOLDING SA, Lausanne (CH)

( * ) Notice: Subject to any disclaimer, the term of this patent is extended or adjusted under 35 U.S.C. 154(b) by 18 days.

(21) Appl. No.: 16/490,990

(22) PCT Filed: Mar. 6, 2018

(86) PCT No.: PCT/IB2018/051430
§ 371 (c)(1),
(2) Date: Sep. 4, 2019

(87) PCT Pub. No.: WO2018/163060
PCT Pub. Date: Sep. 13, 2018

(65) Prior Publication Data
US 2020/0009379 A1    Jan. 9, 2020

(30) Foreign Application Priority Data

Mar. 6, 2017  (CH) .................................... 00272/17

(51) Int. Cl.
*A61N 1/00* (2006.01)
*A61N 1/36* (2006.01)
*A61N 1/04* (2006.01)

(52) U.S. Cl.
CPC ......... *A61N 1/3603* (2017.08); *A61N 1/0452* (2013.01); *A61N 1/0456* (2013.01); *A61N 1/36003* (2013.01)

(58) Field of Classification Search
CPC .............. A61N 1/3603; A61N 1/36014; A61N 1/36034; A61N 1/0452; A61N 1/0456;
(Continued)

(56) References Cited

U.S. PATENT DOCUMENTS

| 116,197 A | 6/1871 | Kidder |
| 3,505,993 A | 4/1970 | Lewes |

(Continued)

FOREIGN PATENT DOCUMENTS

| EP | 0212096 | 3/1987 |
| EP | 2628502 | 8/2013 |
| WO | 2015187426 | 12/2015 |

*Primary Examiner* — Scott M. Getzow
(74) *Attorney, Agent, or Firm* — Graeser Associates International Inc; Dvorah Graeser (57) ABSTRACT

The invention concerns an arrangement comprising an electrical stimulator (1), a programming system (25) for assisting a user in programming it for performing a determined body movement by neuromuscular stimulation; and an input device (24) operable by the user. The programming system is configured to: decompose the neuromuscular movement into distinct actions (31), select one of them, and configuring the electrical stimulator with the electrical stimulation parameters associated with the selected action. The programming system is further configured to select one electrical stimulation parameter among the electrical stimulation parameters associated with the selected distinct action, and, in a cycle performed while the electrical stimulator is connected to the user's body: to receive a value of the selected electrical stimulation parameter through the input device (24); and to configure the electrical stimulator (1) with the received value of the selected electrical stimulation parameter.

20 Claims, 4 Drawing Sheets

(58) Field of Classification Search
CPC ............ A61N 1/36003; A61N 1/37241; A61N 1/37264; A61N 1/36132; A61N 1/37247
See application file for complete search history.

(56) References Cited

U.S. PATENT DOCUMENTS

| | | |
|---|---|---|
| 4,239,046 A | 12/1980 | Ong |
| 4,768,514 A | 9/1988 | De Marzo |
| 5,285,781 A | 2/1994 | Brodard |
| 6,701,189 B2* | 3/2004 | Fang ................. A61N 1/36021 607/48 |
| 2001/0000187 A1 | 4/2001 | Peckham |
| 2002/0188331 A1 | 12/2002 | Fang |
| 2008/0177168 A1 | 7/2008 | Callahan |
| 2008/0288020 A1* | 11/2008 | Einav ................. A61N 1/36003 607/48 |

* cited by examiner

ELECTRICAL STIMULATOR FOR NEUROMUSCULAR STIMULATION

FIELD OF THE INVENTION

The present invention concerns programmable electrical stimulators for stimulation of body tissues, notably electrical stimulators assisting a user in a performance of a determined body movement by neuromuscular stimulation.

DESCRIPTION OF RELATED ART

Electrical stimulators are well known in the state of the art. Electrical stimulators comprise one or more electrical impulse generators, each electrical impulse generator being electrically connected to a physical stimulation channel provided with electrodes for delivering electrical stimulation impulses to muscles and nerves of a user, for example to elicit muscular contractions. Electrical stimulators may deliver electrical stimulation impulses invasively, for example making use of nerve cuff electrodes, or non-invasively, for example making use of surface electrodes.

Electrical stimulators for stimulating a contraction of a single or group of muscles, can be programmed to deliver sequences of electrical stimulation impulses with constant parameters on multiple stimulation channels. These electrical stimulators are provided with a user interface to allow a user or a practitioner to set stimulation parameters, which are generally constituted by a triplet of frequency, current amplitude and duration of the electrical current impulse (e.g. pulse width).

One of the main uses of electrical stimulation in clinical practice is physical therapy, where neuromuscular stimulation is used in order to promote muscle strengthening or to produce a functional movement of a body of a user, i.e. a movement involving a sequence of contractions in one or more muscles resulting in accomplishing a pre-defined task, notably a meaningful functional movements of a paralyzed body part, also in absence of voluntary motor function. These stimulations require a generation of sequences of electrical stimulation impulses synchronized on multiple physical stimulation channels and having stimulation parameters varying in time.

As sequences of electrical stimulation impulses for promoting muscle strengthening or producing a functional movement involve variations of impulse frequencies, current amplitudes and/or duration thereof, often within time intervals shorter than a second, the user or the practitioner is often incapable to manually set up stimulation parameters during the use of the electrical stimulator.

Electrical stimulators are thus typically equipped with a user interface for allowing the user or the practitioner to set up stimulation parameters for configuring each electrical impulse generator for generating a sequence of electrical stimulation impulses providing the desired function.

Some electrical stimulators for physical therapy available on the market (e.g. the Cefar-Compex® Physio 5) provide independent screens that allow the user to customize stimulation sequences by manually selecting the parameters of a stimulation sequence: current amplitude, current pulse-width, stimulation frequency, and their variation across time.

These solutions for determining stimulation parameters of electrical stimulators for stimulating a desired function suffer from major drawbacks, mainly arising from the fact that these solutions target a practitioner that, during a time-consuming phase, repetitively stimulates a user with different stimulation parameters while asking him to provide feedback about stimulated movement and sensations thereof.

These solutions involve time-consuming configuration procedures as the user or practitioner has to explore a vast space of stimulation parameters for determining a set of stimulation parameters capable to stimulate the desired functional movement with a specific electrical stimulator.

These solutions implicitly require that the individual in charge of the configuration procedure has extensive knowledge about electrical stimulation so as to efficiently explore the stimulation parameter space for achieving an efficient configuration, for example by avoiding testing several times unfeasible parameter combinations.

These solutions implicitly require repetitively stimulating a similar movement in the body of the user for iteratively testing subgroup of stimulation parameters so as to determine an optimal set of parameters. Repetitive stimulations of similar movement could induce demotivation and fatigue in the user.

U.S. Pat. No. 6,701,189 B2 describes a system having a plurality of implanted electrical stimulators controlled by a universal external control for selectively perform one or more prosthetic or therapeutic stimulations. Once implanted, each electrical stimulator is exclusively dedicated to a specific function, i.e. a hand-grasp function in upper extremity arm muscles or a standing function in lower extremity arm muscle or a standing function in lower extremity leg muscles and a bladder and bowel control function. The system is equipped with a programming system that allows a clinician to specify the function of interest according to the specific needs of the user and the treatment goal of the clinician.

This system has the limitation of requiring extensive knowledge in electrical stimulation and in-depth knowledge about the physiology of the movements provided by the system, for example about the muscles involved in hand opening/closing. Also, the procedure described in U.S. Pat. No. 6,701,189 B2 results in several additional free parameters, such as the lock state of the stimulation for each available specific function, that make the iterations required in order to setup the system much longer than in above described stimulators.

The invention disclosed in EP1201266A1 describes a graphical user interface for programming a neuromuscular stimulator. The graphical user interface permits a user to define a desired sequence of stimulation impulses for performing a desired movement by means of icons representing stimulation parameters and timing of stimulation sequences. Once the desired sequence is built, it is coded and saved in a memory support, that is then inserted into and read by a neuromuscular stimulator.

This solution has the limitation of requiring extensive knowledge in electrical stimulation, and is prone to lengthy iterations between the guess made during the configuration of the stimulation sequences and the actual execution or testing of the stimulation sequences. For example, if the choice of parameters is not correct at the first attempt, the user is forced to modify the stimulation parameters through the user interface, reprogram the memory support, and iteratively improve the stimulation sequence until satisfactory.

US20140277267 discloses an external control device and method for programming an implantable stimulator. The external control device provides a configuration of an impulse modulation parameter by incrementally increasing his amplitude value up to an awake patient perceived a paraesthesia induced by the stimulation.

Solutions based on US20140277267 suffer not only of the above described drawback but also the additional burden of having to iterate parameters choice every time that the system updates parameters automatically.

U.S. Pat. No. 7,617,002 B2 describes an implantable neuro-stimulator comprising a programming device for setting stimulation parameters. The device executes a parameter configuration search algorithm to guide the clinician in selection of parameters using a decision tree. The decision tree proposes successive values of stimulation parameters until the user confirms a desired physiological effect has been observed, so as to avoid configurations that are unlikely to yield efficacious results.

Solutions based on U.S. Pat. No. 7,617,002 B2 have the limitation of constraining the freedom of the user to explore parameters to simply judging whether a proposed set of parameters is acceptable or not. In practice, procedures of this type may result in lengthy trial-and-error procedures that may never converge to an optimal or even sub-optimal choice of parameters.

The invention disclosed in US20160051817A1 describes an electrical stimulation system able to estimate the electrical resistance of a body portion of a patient so as to generate a constant voltage pulse at a voltage level suitable to stimulate said body portion. The user or the practitioner is allowed to modify the automatically selected stimulation parameters by manually changing the values and combinations of all available parameters of a desired movement. For example, the procedure may require the user or the practitioner to adjust the stimulation amplitude and impulse width of each channel involved in a desired movement while selecting between 1 Hz or 40 Hz stimulation trains.

This solution has the limitation of requiring extensive knowledge in electrical stimulation, and may suffer of the same limitations of conventional commercially available devices whenever the automatic selection of parameters is not acceptable. In practice, most of the times the user will have to perform several iterations in order to find an acceptable set of parameters, resulting in lengthy procedures.

The aim of the invention is to provide an electrical stimulator assisting a user in the execution of a determined (i.e. desired) body movement by neuromuscular stimulation that is devoid, or at least attenuating, drawbacks and limitations of knowns electrical stimulators.

BRIEF SUMMARY OF THE INVENTION

According to the invention, these aims are achieved by means of an arrangement comprising an electrical stimulator of claim 1 and a method of programming an electrical stimulator of claim 17. Dependent claims describe particular embodiments of the invention.

The proposed arrangement and method provide a most efficient and time-saving configuration of the electrical stimulator for stimulating a desired movement than arrangements and methods in the prior art.

The proposed arrangement and method minimizes the number of operations and parameters that the user needs to set for performing a desired movement. In a particular embodiment, the number of parameters to be configured is further reduced by limiting them to a pre-defined subset of parameters.

Moreover, the proposed arrangement and method allow the user to test the movement produced using the stimulation sequences being configured, during the configuration procedure itself, and does not require any more lengthy iterative procedures.

The proposed arrangement and method permit an individual to successfully program the electrical stimulator without prior knowledge on neuromuscular stimulation. The users of the electrical stimulator is thus allowed to configure stimulation sequences to produce complex movements, e.g. configure several stimulation sequences for different stimulation channels, without having prior knowledge of how the stimulation sequences have to be synchronized among themselves.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

The invention concerns an arrangement comprising: an electrical stimulator for neuromuscular stimulation of a body of a user, a programming system for assisting the user in programming the electrical stimulator for performing a determined (i.e. desired) body movement of his body by neuromuscular stimulation; and an input device operable by the user.

Figure 1:
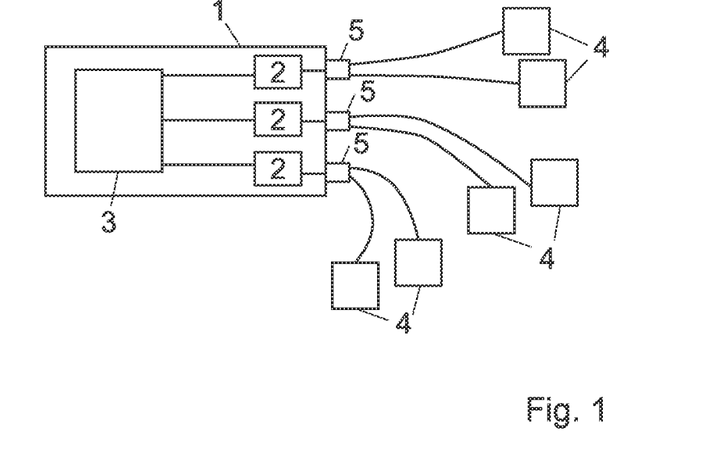
FIG. 1 shows an electrical stimulator for stimulating different portions of a body of a user by means of separate stimulation channels.

As illustrated in FIG. 1, the electrical stimulator 1 comprises a plurality of electrical impulse generators 2 for delivering electrical impulses 8 generated by this plurality of electrical impulse generators 2 to a user muscles and/or nerves through electrodes 4.

The electrical impulse generators are controlled by a controller unit 3. Each electrical impulse generator is electrically connected to a distinct physical stimulation channel 5 provided with electrodes 4 being attachable to the body of the user for stimulating a body movement. The electrodes are connected in pairs to stimulation channels 5.

Figure 2:
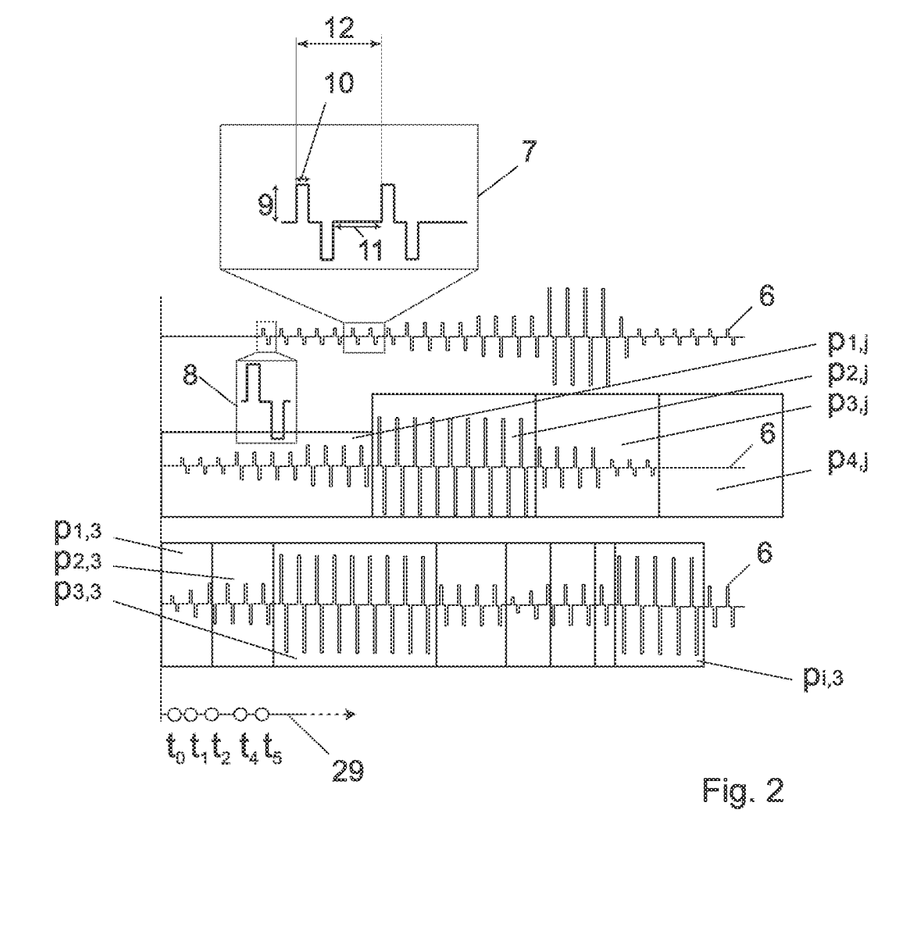
FIG. 2 shows exemplary stimulation sequences generated by the electrical stimulator of FIG. 1.

FIG. 2 shows an example of stimulation sequences 6 for the three stimulation channels 5 illustrated in the exemplary embodiment of FIG. 1. An electrical impulse 8 is magnified in one inlet. A second inlet shows the stimulation parameters of each stimulation impulse train 7 and impulse 8, the current amplitude 9, the duration of the impulse, or pulse-width 6 and the impulse frequency 12, i.e. the number of impulses per seconds or the inverse of the period 11.

Each electrical impulse generator 2 is configured to generate a sequence 6 of electrical stimulation impulses 8 in successive chronological phases $p_i$ according to a group of electrical stimulation parameters.

Each chronological phase $p_i$ comprises (advantageously consists in) one or a plurality of distinct trains 7 of electrical stimulation impulses, each train 7 of electrical stimulation impulses being of a distinct series of successive, identical, equally spaced, electrical stimulation impulses.

Generation of a sequence by means of distinct trains allows the user to control the generation thereof by triggering passages from one chronological phase to another by means of the input device, without any temporal constraints.

Contrary to signals generated by time-variant spaced and/or shaped electrical stimulation impulses, e.g. the intensity of the electrical stimulation impulses is varied at a specific rate in a defined time interval, the sequence is not generated as function of time. Instead, the sequence is generated as function of temporal passages from chronological phases and temporal durations of each chronological phase.

The user can thus generate electrical stimulation impulses according to a train defined by a chronological phase as long as he like, eventually shortening some phases and even reverting to the generation of previous chronological phases.

In fact, the electrical stimulator is configured (notably by means of the controller unit 3) to allow the user to decide for the duration of each phase $p_i$, by letting the user to trigger a passage from a current chronological phase $p_i$ to an adjacent one $p_{i+/-1}$, by means of a user interface, notably by the same input device 24 operable by the user.

In particular, the electrical stimulator is configured to allow the user to decide for the duration of each train of a current phase $p_i$, by letting the user to trigger a passage from a current train to another adjacent one (e.g. by shortening or extending the duration of the train). The adjacent train can be part of the same chronological phase $p_i$ of an adjacent one $p_{i+/-1}$.

This enables the user to perform in part or completely selected movement, in the desired time.

The chronological phases $p_{i,j}$ of each sequence 6 are synchronized together to define a chronological sequence of parts of the desired movement. Each chronological phase $p_i$ defines electrical stimulation impulses for stimulating:
a contraction of a muscle or of a group of muscles to induce a movement to a stationary position of a part of the body of the user;
a relaxation of a muscle or of a group of muscles to induce a movement from a stationary position of part of the body of the user to a relaxed, flaccid, body configuration; or
a contraction or relaxation of a muscle or of a group of muscles to stimulate part of a desired movement of the body of the user.

During a chronological phase $p_i$, a relaxation of a muscle or of a group of muscles is obtained by electrical stimulation impulses that reduce (e.g. attenuate or even remove) a contraction being stimulated by electrical stimulation impulses of the previously chronological phase $p_{i-1}$.

The chronological phases $p_{i,j}$ can be synchronized by means of a stimulation template 29 defining a list of discrete timesteps $t_i$.

The electrical stimulator can thus be configured (notably by means of the controller unit 3) to allow the user to decide for the duration of a current phase $p_{i,j}$ of a sequence j in a synchronized way with the chronological phases of the other sequences by letting the user to trigger a passage from a current timestep $t_i$ to another adjacent (preceding or following) timestep $t_{i+/-1}$, according to the stimulation template 29. The user can trigger the passage by means of a user interface, advantageously by the same input device 24 operable by the user.

Advantageously, the stimulation template 29 is a list of n tuples $T_j=[t,c,i,p,f]$ identified by $j=1, \ldots, n$, where t is the timestep,
c is the stimulation channel,
i is the current amplitude,
p is the pulse-width and
f is the impulse frequency.

The tuple can contain additional information about the electrical stimulation impulses, e.g.
a code identifying a particular waveform of the electrical stimulation impulses (e.g. bipolar, unipolar, square-shaped, triangular-shaped, rounded-shaped, etc.). Each tuple generate identical electrical stimulation impulses that are equally spaced in time.

Every time the stimulation template 29 is executed, i.e. the currently active timestep $t_{active}$ is changed, the controller unit 3 selects one or more tuple of stimulation parameters having the correspondent timestep for the different stimulation channels 5 from the stimulation template 29.

In case no tuple is selected for a stimulation channel, the controller unit can be configured to derive one according to a pre-defined rule.

In one embodiment, the controller is configured to linearly interpolate the stimulation parameters at the active timestep $t_{active}$ from the tuple containing stimulation parameters for the largest $t_1$ and the smallest $t_2$ satisfying $t_1 < t_{active} < t_2$. The current stimulation parameters may be directly computed on-the-fly, retrieving the related stimulation parameters tuple from a data storage mean, or the configuration system used to generate the stimulation template 29 may already generate one tuple for each timestep and stimulation channel of the template 29.

In another embodiment, the controller is configured to apply the stimulating parameters provided by the latest selected tuple. In case a chronological phase requires that the current amplitude, the pulse-width and/or the impulse frequency has to be incremented or decremented from a first to a second value, this chronological phase can be represented by a set of tuples providing intermediate values between the first and the second value. This split the gap from the first to second value to a plurality of smaller gaps so as to smooth the passage from the first to the second value.

The transition from a chronological phase $p_i$ to the following one can thus be triggered by a transition from one timestep to the following one. The transition of one timestep to another is controlled by the user of the electrical impulse generator 2, advantageously trough the input device. In the exemplary illustration of FIG. 2, the chronological phase $p_{2,3}$ of the third sequence 6 of electrical stimulation impulses 8 is triggered by the transition from timestep $t_1$ to timestep $t_2$. As long as the user doesn't actuate a transition to a timestep triggering a transition to another chronological phase, each electrical impulse generator 2 continues to generate electrical stimulation impulses according to electrical stimulation parameters applying for the current chronological phase, i.e. by the electrical stimulation parameters provided by the active Tuples.

The programming system 25 of the arrangement is configured to operate as a configuration system, notably to:
- decompose the desired movement into a finite number of distinct actions, each action being associated to a set of (predefined) values of the electrical stimulation parameters, e.g. defined by a set of distinct tuples being initialized with predefined values;
- select one of said distinct actions, and configuring the electrical stimulator 1 with the electrical stimulation parameters associated with the selected distinct action, i.e. with the set of the predefined values of the electrical stimulation parameters associated with the action (e.g. the set of distinct tuples associated with the selected action);
- select one electrical stimulation parameter among the electrical stimulation parameters associated with the selected distinct action, e.g. one of the parameters of one of the tuple (current amplitude, pulse-width, impulse frequency and waveform) of the set of distinct tuples associated with the selected action.

It is to notice that each action can be performed (entirely or partially) in a simultaneous or sequential way with respect to another one.

The programming system 25 is further configured, in a cycle performed while the electrodes of the electrical stimulator are attached to the user's body, to (preferably automatically):
- receive a value of the selected electrical stimulation parameter through the input device 24; and to
- configure the electrical stimulator 1 with the received value of the selected electrical stimulation parameter to deliver electrical stimulation impulses 8 to the electrodes 4, the electrical stimulation impulses being generated according to the chronological phase $p_{i,j}$ associated to the selected electrical stimulation parameter (e.g. according to the train 7 that is defined by the tuple to which the selected parameters belongs).

In particular, in this cycle, the programming system 25 can be arranged to iteratively configure the electrical stimulator so as to stimulating the user's body by prolonging (a train of) the chronological phase $p_i$ associated to the selected electrical stimulation parameter and using the (latest) received value up to: a new value is provided through the input device 24, a value stimulating the selected action in the user's body is found by the user; and/or a predefined time limit is reached.

Iteratively means that in case a new value is provided by the user, the programming system is arranged to newly configure the electrical stimulator so as to stimulating the user's body by prolonging the same (train of the) chronological phase $p_i$ but using the new received value up to: a new value is provided through the input device 24, a value stimulating the selected action in the user's body is found by the user, and/or the predefined time limit is reached.

In said cycle, the electrical stimulator 1 is configured to immediately generate electrical stimulation impulses in response to a configuration of a parameter value, i.e. to generate electrical stimulation impulses according to the configured values within a time interval that is less than 2 seconds, preferably less than 100 ms, advantageously less than 20 ms.

The immediate stimulation of the user, by electrical stimulation impulses generated according to the value he provided, allows the user and/or the practitioner to observe the effect of the stimulation on the user's body with the provided value.

Advantageously, in said cycle, the programming system 25 is configured to immediately configure the electrical stimulator 1 in response of a reception of said value from the input device, i.e. within a time interval that is less than 2 seconds, preferably less than 100 ms, advantageously less than 20 ms.

Moreover, the immediate configuration and stimulation in response of values provided by the user allows the user to rapidly modify values of the parameters for determining the value that satisfactorily stimulates the selected action in the body of the user.

The configuration and the related stimulation is executed within a time interval less than 100 ms (preferably less than 20 ms). This allows the user to modify the value of the parameters substantially in a continuously way (i.e. perceived by the user as an uninterrupted adaptation of the value) by means of an input device providing uninterrupted outputting of values, i.e. continuously or at least at time intervals less than 100 ms, preferably less than 20 ms.

In particular, the programming system, once the parameter is selected, configures the electrical stimulator with the initially set value of the selected electrical stimulation parameter to generate electrical stimulation impulses according to the train 7 of electrical stimulation impulses to which the selected electrical stimulation parameter is associated. In the above-described cycle, the programming system configures the electrical stimulator with the received value of the selected electrical stimulation parameter to generate electrical stimulation impulses according to the train 7 of electrical stimulation impulses to which the selected electrical stimulation parameter is associated.

This configuration allows the user to adapt the selected electrical stimulation parameter as the electrical stimulator is uniquely generating series of successive, identical, equally spaced, electrical stimulation impulses according to the values provided by the user.

This configuration further allows to reduce the risk of harm to the user as the user is allowed to continually modify the generated electrical stimulation impulses to a desired, comfortable value.

The programming system 25 can be configured to stop the above-described cycle in response to an input provided by the user, advantageously by means of the input device.

The programming system 25 can be configured, automatically or manually, to select every action one at a time to configure or adapt at least one electrical stimulation parameter associated with each action and assist the user in performing the desired movement of the body.

For each selected action, the programming system 25 thus executes the above described steps of: selecting one electrical stimulation parameter, and in said cycle, receiving said value from the input device 24 and configuring the electrical stimulator with the received value.

Each cycle can be interrupted by the user that confirms that the movement produced is satisfactory, e.g. from his visual feedback. The confirmation can be realized via the input device 24, e.g. as previously described.

Alternatively or complementarily, the programming system 25 can be configured to automatically stop each of said cycles. The programming system 25 can be configured, for example, to execute said cycle during a pre-defined time interval. The programming system 25 can be configured, for example, to stop said cycle after a pre-defined time interval is passed from the moment (point in time) a value is received from the input device 24.

The actions can be automatically selected by the programming system 25 according to a chronological order reflecting the chronological concatenation of the actions in said desired body movement.

Figure 3:
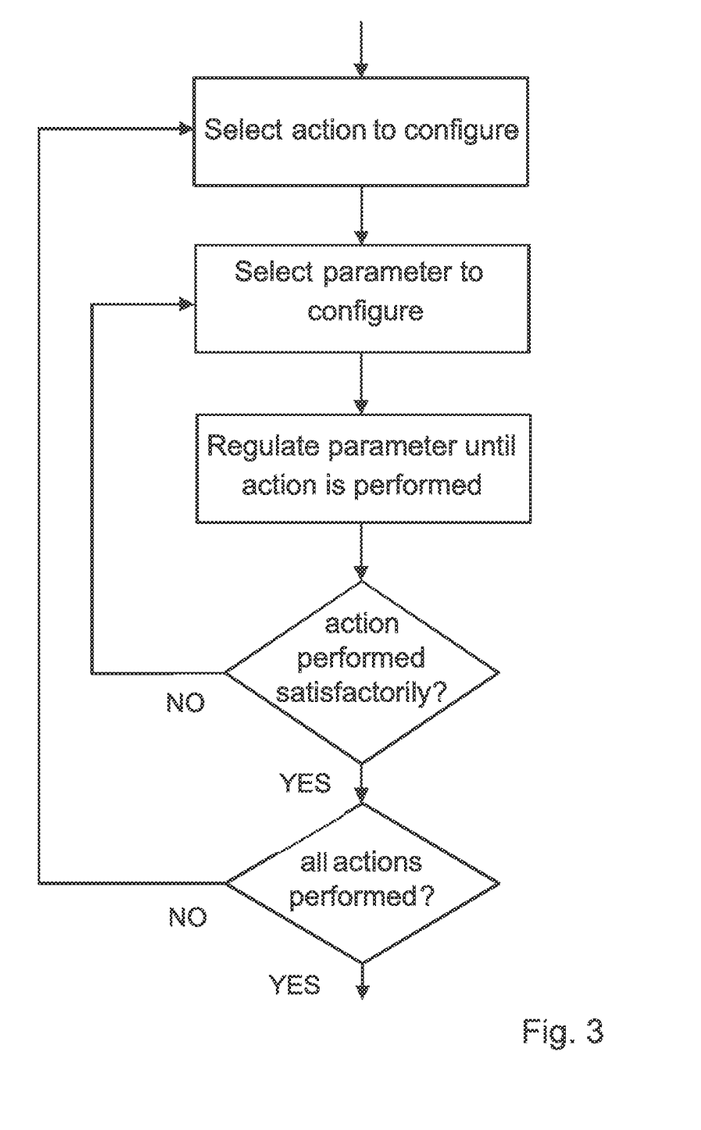
FIG. 3 shows a block diagram illustrating the configuration procedure for programming the electrical stimulator of FIG. 1.

FIG. 3 schematically shows a procedure for programming the electrical stimulator 1 for assisting the user in the performance of a determined body movement that is enabled by the proposed arrangement.

The programming system 25 provides an output to the user, for example by means of an output device 26 of the arrangement for prompting them to select the desired movement: the user selects among a list of potential functional movements that can be realized using the electrical stimulator 1.

Once the user has selected the type of movement via the input device 24, the programming system retrieves the chronological phases ($p_i$) of each sequence 6 of electrical stimulation impulses as function of distinct actions constituting the selected movement.

The programming system can thus be configured to retrieve from a storage means, from the internet, or through any form of data retrieval system a stimulation template 29 that is related to the selected desired movement. At this stage, the stimulation template 29 has a number of parameters that are pre-set, whereas another number of parameter will have to be set by the user during the configuration procedure. The pre-set parameter are determined, for example, based on knowledge of experimented practitioners or based on statistical approach.

The remaining subset of parameters that still need to be set is presented sequentially to the user. Advantageously, the stimulation template 29 carries information defining the order of presentation of parameters that need to be configured to the user. In fact, the order of the parameters to set can impact the quality of the resulting movement, typically in case of functional movement involving a complex contractions of various muscles.

The parameter to be set is presented to the user in form of a distinct action to be performed, the distinct action being part a list of actions constituting the desired movement. Advantageously, the stimulation template 29 can carry information defining the action linked to the parameter to set so as to output it to the user.

Each distinct action can be stimulated by electrical stimulation impulses generated by a single electrical impulse generator.

Advantageously, the electrical stimulator 1 may output stimulation sequences while the user changes a parameter value, varying them according to the variation of the stimulation parameter being regulated by the user through the input device 24. This allows the user to "construct" the movement sequentially, directly observing the effect of parameter variation on a portion of the movement, i.e. on a distinct action, and avoiding to set all the parameters before testing the outcome of the stimulation, i.e. the entire movement, as happens in standard configuration procedures.

The user operates input means 24 of the configuration system 25 to set the value of the parameters. Once the parameter value is set, the user instructs the system to proceed to the next parameter setting or, if no more parameters need to be set, concludes the procedure.

This procedure reduces the complexity of the configuration of the electrical stimulator with respect to a brute force procedure, wherein the user is prompted to:

select a stimulation channel 5 for which the user wants to modify the stimulation sequence 6, to selects the specific stimulation parameter of the selected stimulation channel (such as frequency, pulse width, amplitude, or ramp-up time);

to modify the value of the parameter;

these steps being repeated until the user has "designed" an initially acceptable stimulation sequence 6 for every stimulation channel 5.

In terms of computational complexity of such brute force procedure, the user needs to perform $O(n_p \cdot n_c \cdot k)$ operations, where $n_p$ is the number of parameters that he needs to set, $n_c$ is the number of stimulation channels 5, and k is a number that depends on how skilled the operator is, indicating how often the procedure needs to be repeated.

The programming system 25 reduces the complexity of the configuration procedure to $O(k)$, where k is the number of parameters that the user has to set, and normally $k \ll n_p \cdot n_c \cdot k$.

The predefined order of presentation of configuration parameters facilitates also the user in "seeing" the effects of the electrical stimulation, for example when used to configure a movement produced through functional electrical stimulation. For example, the order may reflect the distal to proximal use of muscles of a movement (or vice versa).

Moreover, the time-steps at which the parameters of stimulation sequences 6 vary are not set by the user but automatically set by the programming system.

In some embodiments, the programming system can automatically set a subset of the parameters based on the content of lookup tables, databases, or other data storage, or retrieve such information from remote systems or from the internet. For example, in certain embodiments of the programming system 25, the timestep of occurrence of each change of parameters can be automatically set fetching the stimulation template 29.

In other embodiments, the programming system 25 can automatically set a fraction of the parameters according to a function of a one or more parameter values presented to the user during the configuration procedure. For example, in certain embodiments of the invention, the programming system can ask the user to only set the maximum current amplitude to generate a "ramp-up" of stimulation impulses, i.e. current amplitudes growing from a minimum up to a maximum value in a predetermined amount of time. Once this value is set by the user, the system interpolates intermediate ramp-up values without explicitly querying the user to specify ramp-up duration or manually design the ramp.

In one embodiment, the programming system 25 can limit the parameter to be set to a subset of the parameters defining the amplitudes of electrical impulses, while automatically set the others parameters according to statistically derived pre-defined values.

The input device comprises a physical or virtual manipulating element configured to be manipulated by fingers of a single hand of the user. This allows a user for programming and executing a desire movement on his arm or hand by generating input (e.g. parameters value or timestep increments) by manipulating the input device with fingers of the free hand.

In one embodiment, the input device comprises a physical manipulating element being moveable or pivotally mounted so as his free extremity is movable along a line in response of a movement performed by the fingers of the user. Alternatively, the input device can comprise a virtual manipulating element being moveable along a line in response of a touch of the fingers of the user on a surface of the input device.

This input device allows a user to comfortably control the programming and the execution of stimulation as parameters values and timestep increment can be rapidly generated and adapted by simply actuating the manipulating element along the line.

More advantageously, the manipulating element can be physically or virtually rotatable around a physical or virtual axis in response of a movement performed by the fingers on said physical or virtual manipulating element.

This input device allows the user to comfortably and precisely control the programming and the execution of stimulation as parameters values and timestep increment can be rapidly and precisely generated as the infinitely rotating manipulating element can provide both a smaller minimal increment and a broader range than a linear one.

Figure 4:
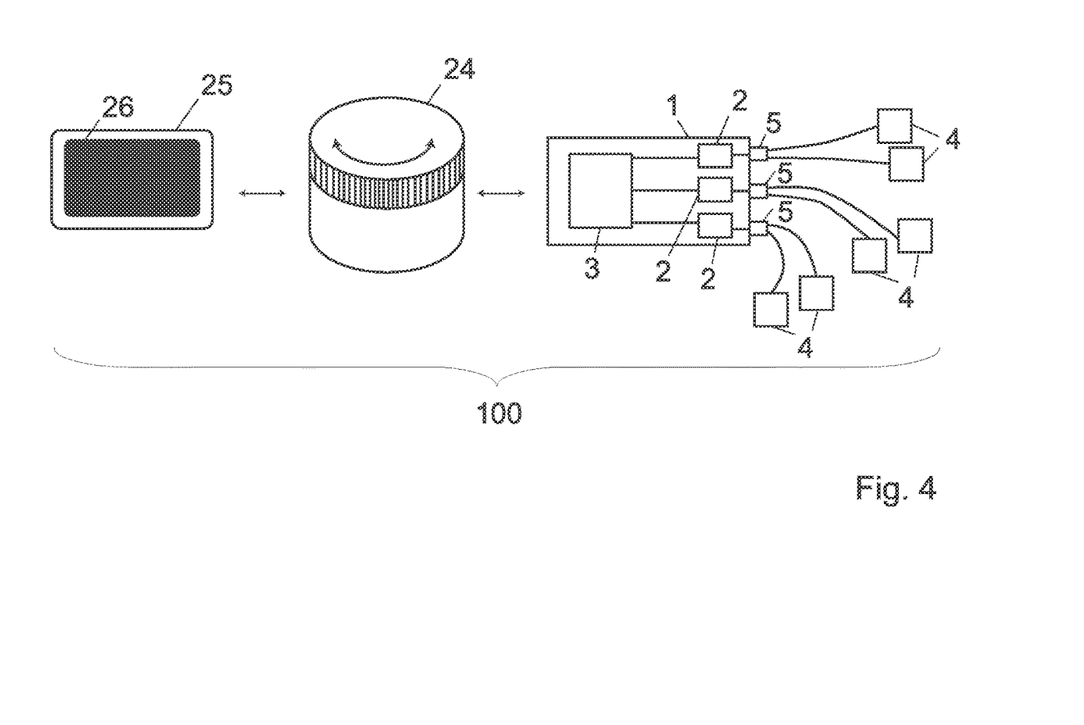
FIG. 4 shows an embodiment of an arrangement comprising the electrical stimulator of FIG. 1, a programming system and an input means. The input means is in form of a control knob used both to configure the stimulation template parameters and to control the generation of stimulation sequences.

In the preferred embodiment of FIG. 4, the input device has a form of a wireless input device 24. The wireless device comprises a rotational control knob that is used both to set the parameter values during the programming procedure and stepping the active timestep of a stimulation sequence during the use of the electrical stimulator 1. Parameters to be set are presented to the user on the output mean 26 being integrated in the programming device 25, such as a display 26 of a tablet 25.

Figure 5A:
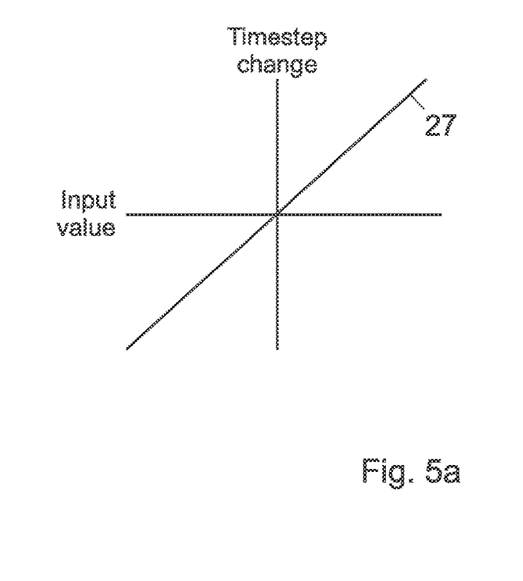
FIG. 5a shows a first embodiment of a relationship between a value provided by the input mean and a timestep increase/decrease used for selecting one of the trains of electrical stimulation impulses of a stimulation sequence.

The control knob 24 can be used to set the stimulation parameters during the configuration procedure and to change the active step with a linear function 27 depending on the rotation of the control knob 24, as illustrated in FIG. 5a. The linear function 27 defines the positive (or negative) number of timestep to add (or subtract) to the current active timestep when the knob is rotated by a certain angle, generating an input value to the controller unit.

Alternatively, the control knob 24 can be configured to generate input values that influence the speed at which the controller unit 3 of the electrical stimulator 1 automatically steps the active timestep. Input values and related changes in speed are positive for a rotation in one direction, and negative for a rotation in another direction.

Figure 5B:
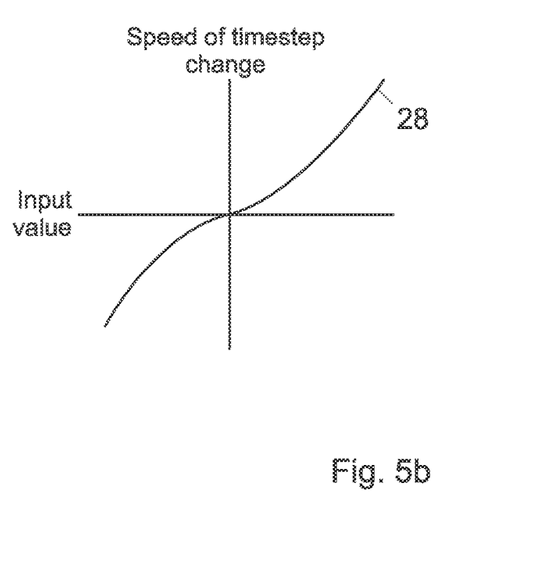
FIG. 5b shows a second embodiment of a relationship between a value provided by the input mean and a timestep increase/decrease used for selecting one of the trains of electrical stimulation impulses of a stimulation sequence.

In a preferred embodiment of the present invention the mapping of the input mean value to the timestep stepping is linear. In other embodiments of the present invention the mapping of the input value to timestep stepping or speed of timestep change can be non-linear (e.g. FIG. 5b), or dynamically adapted during the execution of the stimulation sequence.

Figure 6:
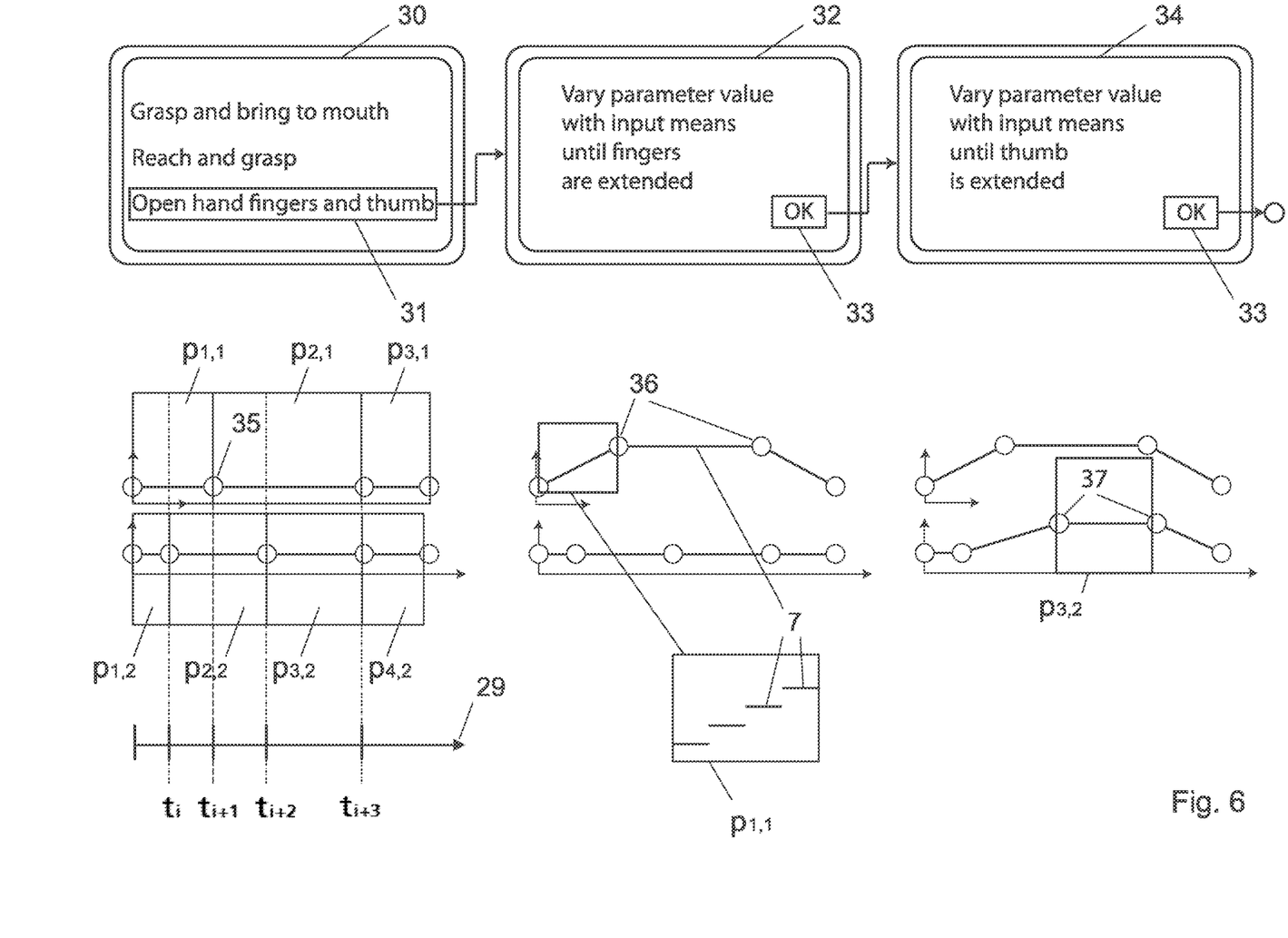
FIG. 6 shows an exemplary sequence of displayed screens on an output means of the programming system, in this case a tablet, through which the user is guided automatically by the configuration system 25.

FIG. 6 shows an exemplary scenario where the user is guided for programming the electrical stimulator trough messages displayed by the output means 26 in order to set the stimulation parameters that are required to produce a functional movement of interest. First, the user selects among a list of possible functional movements on the display 30. Once the selection has been made, the system automatically loads the stimulation template 29 corresponding to the selected movement. For simplicity, in our representation the stimulation template 29 is shown as a number of stimulation parameters tuples 35, visualized on two timestep-to-current-amplitude coordinate systems, for the two stimulation channels needed to reproduce such movement. Each tuple of the stimulation template 29 describes the beginning of a chronological phase $p_i$ or the beginning of an intermediate part thereof. The timesteps are represented on the x-axis, the stimulation amplitude on the y-axis for the two different stimulation channels. Several stimulation parameters—namely the timesteps at which the train of stimulation impulses 7—will have to be adapted by the user. The number of stimulation channels to be configured is already pre-set by the configuration system 25.

The programming system 25 proposes a first configuration step, displayed by screen 32 wherein it asks to the user to vary a parameter using the input mean 24 until the user is satisfied with the produced movement of the specific body portion. Confirmation button 33 is used to indicate that a produced movement is satisfactory, for example as soon as the stimulation produces a full finger extension while configuring a reach-and-grasp action. Once the parameter has been set, the configuration system 25 modifies one or more stimulation tuples 35 to reflect the parameter selection. In this example, the configuration system 25 modifies the current amplitude of the tuples 36.

Next, the programming system 25 proposes a second configuration step, displayed in screen 34 wherein the user needs to use the input mean 24 to vary a second parameter, for example the stimulation amplitude on the second stimulation channel 5. Once the second parameter is set, the programming system 25 modifies one or more stimulation tuples 35 to reflect the parameter selection. In this example, the configuration system 25 modifies the current amplitude of the tuples 37.

After the second parameter is set, the stimulation template 29 is fully configured and the user can proceed to executing the stimulation template 29, which will produce the same movement produced during the configuration phase Advantageously, an additional screen can be presented between the screen 30 and 32, showing the placement of electrodes on the body of the user to produce the desired movement. The placement can be represented through a photo of the electrode placement, a 2D model or a 3D model of the human body, and allows users without knowledge of electrical stimulation to operate the system.

Advantageously, the programming system can propose one or more steps of the assisted calibration procedure multiple times during a single calibration procedure according to global metrics of the produced movement. Global metrics of the produced movement may refer to subjective rankings, such as measures of comfort and/or quality, or to subjective sensor readings, such as body part kinematic and dynamics, biophysical responses, proximity to predefined objects.

The invention further concern a method of programming the electrical stimulator 1 for assisting the user in the performance of a determined body movement that is enabled by the proposed arrangement.

The method comprises the steps selecting one of distinct actions forming the desired neuromuscular movement, and configuring the electrical stimulator 1 with the electrical stimulation parameters associated with the selected distinct action.

The method comprises providing the electrical stimulator 1 and attaching the electrodes to the user's body;

The method comprises a step of decomposing the desired neuromuscular movement into a finite number of distinct actions, each action being associated to a set of values of the electrical stimulation parameters.

The method then comprises a step of selecting one electrical stimulation parameter among the electrical stimulation parameters associated with the selected distinct action, and, in a cycle performed while the user attempts to execute the selected distinct action:

receiving a value of the selected electrical stimulation parameters through an input device of the electrical stimulator, operated by said user; and configuring the electrical stimulator with the received value of the selected electrical stimulation parameter.

LIST OF REFERENCE NUMERALS

1 Electrical stimulator
2 Impulse generator
3 Controller unit
4 Electrodes
5 Stimulation channel
6 Stimulation sequence
7 Train of stimulation impulses
8 Electrical stimulation impulse
9 Current amplitude
10 Current pulse-width
11 Stimulation period
12 Stimulation frequency
24 Input means
25 Configuration system
26 Output means
27 Input means-to-timesteps change transfer function
28 Input means-to-timesteps change speed of timesteps stepping transfer function
29 Stimulation template
30 Configuration screen
31 Selected movement
32 Parameter Configuration screen (fingers)
33 Confirmation button
34 Parameter Configuration screen (thumb)
35 Stimulation parameter tuple
36 Tuples changed by the step of screen 32
37 Tuples changed by the step of screen 33 100 Arrangement for neuromuscular stimulation
$t_0, t_1 \ldots t_i$ initial, $1^{st}, \ldots i^{th}$ time step
$p_{i,j}$ $i^{th}$ chronological phase of channel j

The invention claimed is:

1. An arrangement comprising:
an electrical stimulator for neuromuscular stimulation;
a programming system for assisting a user in programming the electrical stimulator for performing a desired body movement by neuromuscular stimulation; and
an input device operable by said user;
wherein said electrical stimulator comprises a plurality of electrical impulse generators each electrically connected to a physical stimulation channel provided with electrodes for stimulating a body movement,
each electrical impulse generator being configured to generate a sequence of electrical stimulation impulses in successive chronological phases according to a group of electrical stimulation parameters;
wherein the programming system is configured to:
decompose said desired body movement into a finite number of distinct actions, each action being associated to a set of values of the electrical stimulation parameters;
select one of said distinct actions, and configure the electrical stimulator with the electrical stimulation parameters associated with the selected distinct action;
select one electrical stimulation parameter among the electrical stimulation parameters associated with the selected distinct action, and, in a cycle performed while the electrodes of the electrical stimulator are connected to the user's body to:
receive a value of the selected electrical stimulation parameter from the input device of the electrical stimulator;

configure the electrical stimulator with the received value of the selected electrical stimulation parameter to deliver electrical stimulation impulses to said electrodes according to the chronological phase associated to the selected electrical stimulation parameter.

2. The arrangement according to claim 1, wherein said input device is arranged to provide a series of successive, distinct values at a frequency bigger than 1 Hz in response of a manipulation of the user.

3. The arrangement according to claim 1, wherein said electrical stimulation parameters define waveform, amplitude, impulse width and/or impulse frequency of electrical stimulation impulses generated in each of said chronological phases.

4. The arrangement according to claim 1, wherein electrical impulses generated in each chronological phase ($p_i$) comprise one or a plurality of distinct trains of electrical stimulation impulses, each train of electrical stimulation impulses being of a series of successive, identical, equally spaced, electrical stimulation impulses.

5. The arrangement according to claim 4, wherein the programming system is arranged, in said cycle, to configure the electrical stimulator to generate electrical stimulation impulses according to the train of electrical stimulation impulses that is associated with the selected electrical stimulation parameter.

6. The arrangement according to claim 1, wherein the programming system is configured to select said one electrical stimulation parameter within a pre-defined subgroup of stimulation parameters within the electrical stimulation parameters associated with the selected distinct action.

7. The arrangement according to claim 6, wherein the programming system is configured to automatically infer another electrical stimulation parameter from said received value, said other electrical stimulation parameters belonging to the same chronological phase ($p_i$) and associated with another train of electrical stimulation impulses of the same chronological phase ($p_i$).

8. The arrangement according to claim 6, wherein the programming system is configured to automatically assign said received value to another electrical stimulation parameter, said other electrical stimulation parameters belonging to a chronological phase ($p_i-1$, $p_i+1$) that is chronologically adjacent to the chronological phase ($p_i$) associated with the selected electrical stimulation parameter and said another electrical stimulation parameter belonging to a train of electrical stimulation impulses of said adjacent chronological phase ($p_i-1$, $p_i+1$).

9. The arrangement according to claim 1, wherein said selected electrical stimulation parameter and/or the electrical stimulation parameters of said pre-defined subgroup of stimulation parameters define uniquely amplitudes of electrical impulses.

10. The arrangement according to claim 1, wherein the input device comprises a physical or virtual manipulating element configured to be manipulated by fingers of a single hand of the user; the input device being configured to generate a value in response of a movement performed by said fingers on said physical or virtual manipulating element.

11. The arrangement according to claim 10, the manipulating element being physically or virtually movable along a line in response to a movement performed by said fingers on said physical or virtual manipulating element;
the input device being configured to generate a value as function of a relative positioning of said manipulating element, a speed of a relative movement of said manipulating element, a direction of a relative movement of said manipulating element and/or a duration time said manipulating element being on a predefined relative positioning.

12. The arrangement according to claim 11, the manipulating element being physically or virtually rotatable around a physical or virtual axis in response of a movement performed by said fingers on said physical or virtual manipulating element;
the input device being configured to generate a value as function of a rotational speed of a rotation of said manipulating element, a direction of a rotation of said manipulating element and/or a duration time said manipulating element being on a predefined relative angular positioning.

13. The arrangement according to claim 1, further configured so a transition from one of said chronological phases ($p_i$) to another one is triggered by an input provided by said input device.

14. The arrangement according to claim 1, wherein the programming system is configured to perform said cycle automatically.

15. The arrangement according to claim 14, wherein the programming system is further configured to
receive a selection input from the input device, and to select said one of said distinct actions and/or said one stimulation parameter based on said selection input.

16. The arrangement according to claim 1, wherein the programming system is configured to stop said cycle in response to an input from the input device.

17. A method of programming an electrical stimulator for assisting a user in the performance of a desired body movement by neuromuscular stimulation, comprising:
providing an electrical stimulator comprising a plurality of electrical impulse generators each electrically connected to a physical stimulation channel provided with electrodes for stimulating the body movement, each electrical impulse generator being configured to generate a sequence of electrical stimulation impulses in successive chronological phases according to a group of electrical stimulation parameters;
attaching said electrodes to the user's body;
decomposing said desired body movement into a finite number of distinct actions, each action being associated to a set of values of the electrical stimulation parameters;
selecting one of said distinct actions, and configuring the electrical stimulator with the electrical stimulation parameters associated with the selected distinct action;
selecting one electrical stimulation parameter among the electrical stimulation parameters associated with the selected distinct action, and, in a cycle performed while the user attempts to execute the selected distinct action:
receiving a value of the selected electrical stimulation parameters through an input device of the electrical stimulator, operated by said user;
configuring the electrical stimulator with the received value of the selected electrical stimulation parameter.

18. The method of claim 17, wherein the electrical generator is programmed to perform said cycle automatically.

19. The method of claim 17, further comprising successively selecting all said actions one at a time, so as to execute said steps of: selecting one electrical stimulation parameter, and in said cycle, receiving
said value and configuring the electrical stimulator with the received value.

20. The method of claim 19, said actions being automatically selected according to a chronological order reflecting the chronological concatenation of the actions in said desired body movement.

* * * * *